US012746372B2

(12) United States Patent
Uto et al.

(10) Patent No.: US 12,746,372 B2
(45) Date of Patent: Sep. 29, 2026

(54) BALLOON CATHETER

(71) Applicant: KANEKA CORPORATION, Osaka (JP)

(72) Inventors: Toshihiko Uto, Settsu (JP); Shintaro Osumi, Settsu (JP); Hironori Takata, Settsu (JP)

(73) Assignee: KANEKA CORPORATION, Osaka (JP)

( * ) Notice: Subject to any disclaimer, the term of this patent is extended or adjusted under 35 U.S.C. 154(b) by 1039 days.

(21) Appl. No.: 17/908,682

(22) PCT Filed: Feb. 24, 2021

(86) PCT No.: PCT/JP2021/006827
§ 371 (c)(1),
(2) Date: Sep. 1, 2022

(87) PCT Pub. No.: WO2021/177103
PCT Pub. Date: Sep. 10, 2021

(65) Prior Publication Data
US 2023/0118963 A1 Apr. 20, 2023

(30) Foreign Application Priority Data
Mar. 6, 2020 (JP) ................................ 2020-039082

(51) Int. Cl.
*A61M 25/10* (2013.01)
*A61N 5/067* (2006.01)

(52) U.S. Cl.
CPC ............. *A61M 25/10* (2013.01); *A61N 5/067* (2021.08); *A61M 2025/1043* (2013.01)

(58) Field of Classification Search
CPC .......... A61M 25/10; A61M 2025/1043; A61M 25/1006; A61N 5/067; A61N 2005/0609;
(Continued)

(56) References Cited

U.S. PATENT DOCUMENTS 5,090,959 A * 2/1992 Samson ................. A61B 1/042 600/116
5,304,171 A * 4/1994 Gregory ............... A61B 18/245 606/7
(Continued)

FOREIGN PATENT DOCUMENTS

JP 7-124260 A 5/1995
JP H0889499 A * 4/1996
(Continued)

OTHER PUBLICATIONS

JPH0889499A Translation (Year: 1996).*
(Continued)

*Primary Examiner* — Niketa Patel
*Assistant Examiner* — Attiya Sayyada Hussaini
(74) *Attorney, Agent, or Firm* — Birch, Stewart, Kolasch & Birch, LLP

(57) ABSTRACT

A balloon catheter (1) comprising: a first shaft (10) having a first lumen (11) and a second lumen (12); a second shaft (20) located distal to the first shaft (10); a balloon (30) located distal to the second shaft (20); and an optical fiber (40) disposed inside the balloon (30); wherein: the first shaft (10) is made of a resin; a cross-sectional area of the resin forming the first shaft (10) is larger than a cross-sectional area of either the first lumen (11) or the second lumen (12), which has a larger cross-sectional area, in a cross section perpendicular to a longitudinal direction; the optical fiber (40) is joined to a distal end (11*d*) of the first lumen (11); a proximal end (30*p*) of the balloon (30) is joined to the second shaft (20); and a distal end (30*d*) of the balloon (30) is joined to the optical fiber (40).

14 Claims, 4 Drawing Sheets

(58) Field of Classification Search
CPC .............. A61N 2005/063; A61N 5/062; A61N 2005/0632; A61N 5/0601–0603; A61N 2005/0602–0612
See application file for complete search history.

(56) References Cited

U.S. PATENT DOCUMENTS

| | | | | |
|---|---|---|---|---|
| 5,891,082 | A | 4/1999 | Leone et al. | |
| 5,947,927 | A | 9/1999 | Mertens | |
| 5,997,570 | A | 12/1999 | Ligtenberg et al. | |
| 5,997,571 | A * | 12/1999 | Farr | A61N 5/0601 606/7 |
| 6,613,066 | B1 | 9/2003 | Fukaya et al. | |
| 7,783,338 | B2 * | 8/2010 | Ainsworth | A61B 5/6853 604/96.01 |
| 8,864,705 | B2 * | 10/2014 | Nishigishi | A61M 25/104 604/103.09 |
| 2003/0208221 | A1 * | 11/2003 | El-Nounou | A61M 25/104 606/191 |
| 2004/0059277 | A1 * | 3/2004 | Maguire | A61M 25/10 604/104 |
| 2004/0092830 | A1 | 5/2004 | Scott et al. | |
| 2004/0093044 | A1 | 5/2004 | Rychnovsky et al. | |
| 2008/0221458 | A1 | 9/2008 | Scott et al. | |
| 2012/0226231 | A1 | 9/2012 | Nishigishi | |

FOREIGN PATENT DOCUMENTS

| | | | |
|---|---|---|---|
| JP | 8-317991 | A | 12/1996 |
| JP | 2002-507460 | A | 3/2002 |
| JP | 2005-534409 | A | 11/2005 |
| JP | 2008-264134 | A | 11/2008 |
| JP | 2009-160446 | A | 7/2009 |
| JP | 2012-183127 | A | 9/2012 |

OTHER PUBLICATIONS

International Search Report, issued in PCT/JP2021/006826, dated May 11, 2021.

International Search Report, issued in PCT/JP2021/006827, dated May 11, 2021.

* cited by examiner

[Fig. 2]

[Fig. 4]
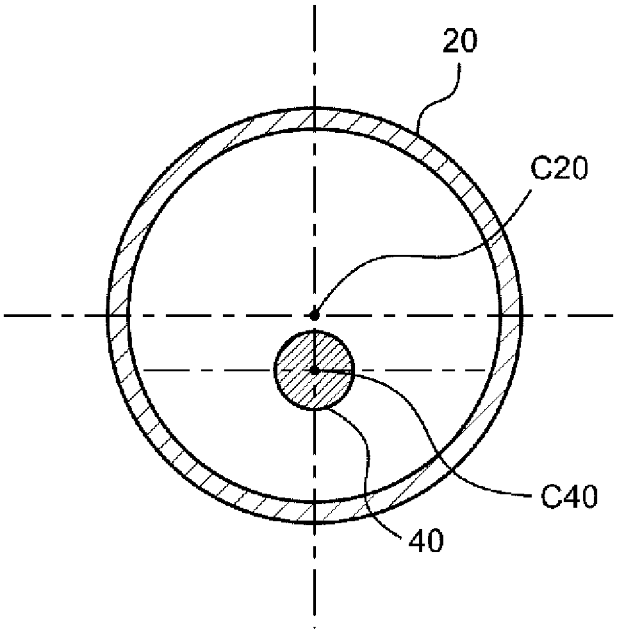
[Fig. 5]
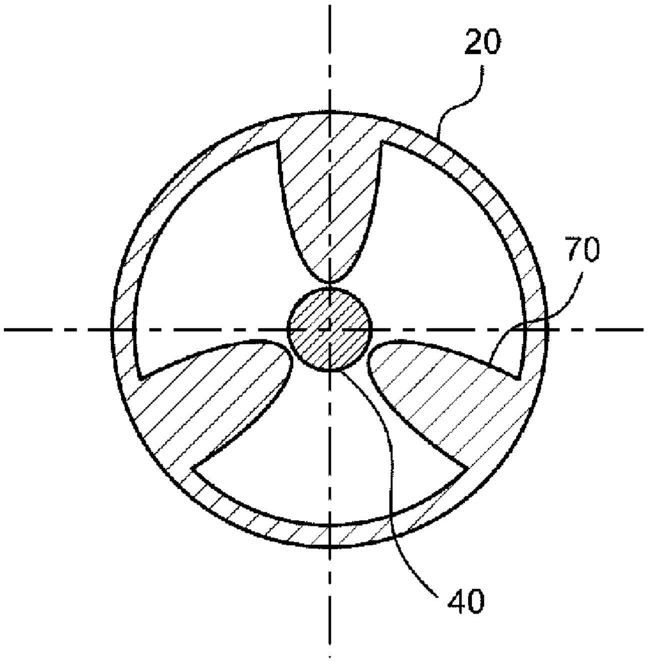

BALLOON CATHETER

TECHNICAL FIELD

The present invention relates to a balloon catheter, which is used when irradiating a tissue such as cancer cells with light in an internal lumen such as a blood vessel and a gastrointestinal tract.

BACKGROUND ART

In photodynamic therapy (PDT), a photosensitizer is administered into a human body by intravenous injection or intraperitoneal administration, and the photosensitizer is accumulated in a target tissue such as cancer cells, and light of a specific wavelength is applied to the target tissue to excite the photosensitizer. When the excited photosensitizer returns to a ground state, energy conversion occurs to generate reactive oxygen species. This reactive oxygen species attack the target tissue, whereby the target tissue can be removed. In ablation (tissue ablation) using laser light, the target tissue is irradiated with laser light to be cauterized.

A light irradiation medical device is used for irradiating a treatment site, which is a target tissue such as cancer cells, with light of a specific wavelength in an internal lumen such as a blood vessel and a digestive tract in ablation using PDT or laser light. In the light irradiation medical device, an optical fiber is placed in a tube of a catheter for irradiating a target tissue with light.

The light irradiation medical device may be delivered to a treatment site alone, however, it is generally used together with a catheter or an endoscope for delivery. In endoscopic treatment, the light irradiation medical device is placed in a human body through a forceps opening of an endoscope so that it extends from a distal side of the forceps opening of the endoscope, and delivered to a treatment site.

For example, Patent Literature 1 discloses a balloon catheter comprising a tube-like basic body with a distal and a proximal end, and a balloon member arranged at the distal end surrounding an end-section of the basic body, a light conductor extending from the proximal to the distal end, and having close to the distal end a light-emitting end-section situated inside the balloon member, said light-emitting end-section being fixed to the basic body, wherein the light conductor extends through a lumen of the basic body and wherein an outer wall of the end-section of the basic body extending into the balloon member and bounding the lumen has at least partially been removed so as to expose said end-section of the light conductor, and describes that an optical fiber is used for the light-emitting end-section.

Patent Literature 2 discloses a guidance catheter for laser fiber, wherein a shaft comprises an inner tube and an outer tube, a balloon is disposed at a distal end of the outer tube, the inner tube is arranged so as to extend from a rear of the outer tube through an inside of the balloon to a distal end of the balloon, a lumen into which a laser fiber can be inserted is provided at least in the inner tube, a laser fiber insertion port is formed at a rear end of the outer tube, a light sensitive substance is fixed on an outer circumference of the balloon, one positioning marker is provided on an outer circumference of the inner tube at the center of the balloon or two positioning markers are provide on the outer circumference of the inner tube on both sides of the balloon at equal intervals from the center of the balloon, and a laser fiber stopper is provided in the inner tube at the center of the balloon so that a distal end of the laser fiber stops at the center of the balloon.

CITATION LIST

Patent Literature

Patent Literature 1
Japanese Unexamined Laid-open Patent Application Publication No. H8-317991
Patent Literature 2
Japanese Unexamined Laid-open Patent Application Publication No. 2009-160446

SUMMARY OF INVENTION

Technical Problem

However, in the balloon catheters of Patent Literatures 1 and 2, when pulling the balloon catheter toward a hand side to remove it from an endoscope or the like, the force for pulling the balloon catheter toward the hand side is not easily transmitted to a distal end of the balloon. Therefore, there was a problem that it was difficult to remove the balloon catheter from an endoscope.

Further, in the balloon catheters of Patent Literatures 1 and 2, when the balloon catheter is placed in a bent internal lumen, the optical fiber also bends. In addition, when placing the balloon catheters of Patent Literatures 1 and 2 in an internal lumen, the balloon is restrained in the internal lumen, and the optical fiber is bent also in the case where the balloon is compressed and its length in the axial direction is shortened. Therefore, the position of the optical fiber placed inside the balloon deviates from a center of the balloon in a cross section perpendicular to the longitudinal direction, and as a result, there was a problem that the target tissue could be sufficiently irradiated with light so that photodynamic therapy could not be sufficiently performed or the target tissue was irradiated with light stronger than expected so that the internal tissue may be perforated.

The present invention has been made in view of the above circumstances, and an object the present invention is to provide a balloon catheter that can be easily removed from an endoscope or the like and allows an optical fiber to be arranged at a center of the balloon in a cross section perpendicular to the longitudinal direction even when a shaft is bent or the balloon is compressed.

Solution to Problem

A first balloon catheter, which solves the above problem, comprises: a first shaft having a first lumen and a second lumen; a second shaft located distal to the first shaft; a balloon located distal to the second shaft; and an optical fiber disposed inside the balloon; wherein: the first shaft is made of a resin; a cross-sectional area of the resin forming the first shaft is larger than a cross-sectional area of either the first lumen or the second lumen, which has a larger cross-sectional area, in a cross section perpendicular to a longitudinal direction; the optical fiber is joined to a distal end of the first lumen; a proximal end of the balloon is joined to the second shaft; and a distal end of the balloon is joined to the optical fiber.

A second balloon catheter, which solves the above problem, comprises: a first shaft provided with an inner tube having a first lumen, and having a second lumen; a second shaft located distal to the first shaft; a balloon located distal to the second shaft; and an optical fiber disposed inside the balloon; wherein: at least a part of an outer surface of the inner tube is fixed to an inner surface of the first shaft; the optical fiber is joined to a distal end of the inner tube; a proximal end of the balloon is joined to the second shaft; and a distal end of the balloon is joined to the optical fiber.

In the balloon catheter of the present invention, it is preferable that a length of the second shaft in the longitudinal direction is 10 times or more a minimum outer diameter of the second shaft.

In the balloon catheter of the present invention, it is preferable that a position of a central axis of an outer shape of the second shaft is different from a position of a central axis of an outer shape of the optical fiber in a cross section perpendicular to the longitudinal direction at a proximal end of the second shaft.

In the balloon catheter of the present invention, it is preferable that an area of a gap between an inner surface of the second shaft and an outer surface of the optical fiber is 40% or more of an area of a lumen of the second shaft in a cross section perpendicular to the longitudinal direction of the second shaft.

In the balloon catheter of the present invention, it is preferable that a protrusion which comes into contact with an outer surface of the optical fiber is provided on an inner surface of the second shaft.

In the balloon catheter of the present invention, it is preferable that a tip piece is provided on a distal side of the optical fiber, and a distal end of the tip piece is located distal to the distal end of the balloon.

Advantageous Effects of Invention

According to the first balloon catheter of the present invention, since the cross-sectional area of the resin forming the first shaft is larger than the cross-sectional area of either the first lumen or the second lumen, which has a larger cross-sectional area, in a cross section perpendicular to the longitudinal direction, the optical fiber is joined to the distal end of the first lumen, the proximal end of the balloon is joined to the second shaft, and the distal end of the balloon is joined to the optical fiber, the force applied to the balloon catheter is easily transmitted to both the proximal end and the distal end of the balloon. Therefore, it is possible to improve removability of the balloon catheter from an endoscope or the like. In addition, since the optical fiber is joined to the distal end of the first lumen, that is not the proximal end of the balloon and is located proximal to the proximal end of the balloon, the optical fiber is not fixed to another object between the distal end of the balloon and the distal end of the first lumen in the longitudinal direction, and is able to move freely. As a result, the optical fiber can be arranged at a center of the balloon in the cross section perpendicular to the longitudinal direction, even in the state where the shaft of the balloon catheter is bent or the balloon is compressed.

According to the second balloon catheter of the present invention, since the first shaft is provided with the inner tube having the first lumen and has second lumen, at least a part of the outer surface of the inner tube is fixed to the inner surface of the first shaft, the optical fiber is joined to the distal end of the inner tube, the proximal end of the balloon is joined to the second shaft, and the distal end of the balloon is joined to the optical fiber, the force for pulling the balloon catheter is easily transmitted to both the proximal end and the distal end of the balloon when the balloon catheter is removed from an endoscope or the like, which makes it easier to remove the balloon catheter from an endoscope or the like. Further, since the optical fiber is joined to the distal end of the inner tube, the optical fiber is able to move freely in the range between the distal end of the balloon and the distal end of the first lumen in the longitudinal direction. As a result, the optical fiber can be arranged at a center of the balloon in the cross section perpendicular to the longitudinal direction, even in the state where the shaft of the balloon catheter is bent or the balloon is compressed.

BRIEF DESCRIPTION OF DRAWINGS

FIG. 4 shows a cross-sectional view taken along a line IV-IV of the balloon catheter shown in FIG. 3.

FIG. 5 shows a cross-sectional view of a second shaft along a direction perpendicular to the longitudinal direction in a balloon catheter according to another embodiment of the present invention.

DESCRIPTION OF EMBODIMENTS

Figure 1:
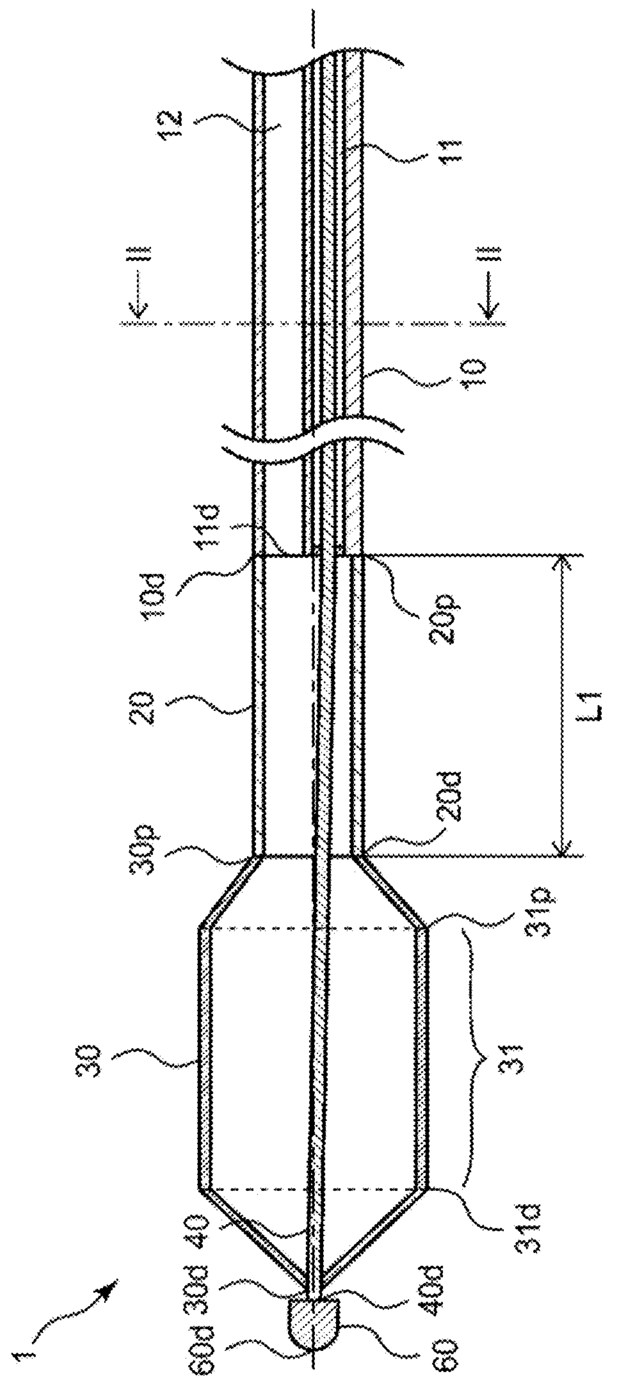
FIG. 1 shows a cross-sectional view of a first balloon catheter along a longitudinal direction according to an embodiment of the present invention.

Hereinafter, the present invention is specifically described below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

First, a first balloon catheter of the present invention is explained.

Figure 2:
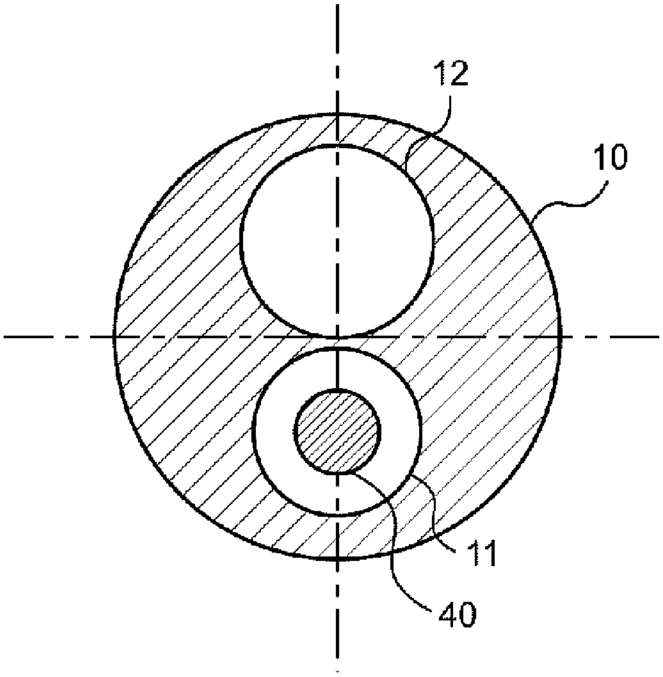
FIG. 2 shows a cross-sectional view taken along a line II-II of the balloon catheter shown in FIG. 1.

FIG. 1 shows a cross-sectional view of a first balloon catheter 1 along a longitudinal direction according to an embodiment of the present invention, and FIG. 2 shows a cross-sectional view taken along a line II-II, that is perpendicular to the longitudinal direction, of the balloon catheter 1 shown in FIG. 1. As shown in FIG. 1, a balloon catheter 1 of the present invention comprises a first shaft 10 having a first lumen 11 and a second lumen 12, a second shaft 20 located distal to the first shaft 10, a balloon 30 located distal to the second shaft 20, and an optical fiber 40 disposed inside the balloon 30, wherein the optical fiber 40 is joined to a distal end **11*d* of the first lumen 11, a proximal end 30*p* of the balloon 30 is joined to the second shaft 20, and a distal end 30*d* of the balloon 30 is joined to the optical fiber 40. Further, the first shaft 10 is made of a resin, and as shown in FIG. 2, a cross-sectional area of the resin forming the first shaft 10 is larger than a cross-sectional area of either the first lumen 11 or the second lumen 12, which has larger cross-sectional area, in a cross section perpendicular to the longitudinal direction. That is, the cross-sectional area of the resin forming the first shaft 10 is larger than the larger of the cross-sectional area of the first lumen 11 and the cross-sectional area of the second lumen 12. In other words, the cross-sectional area of the resin forming the first shaft 10 is larger than the cross-sectional areas of both the first lumen 11 and the second lumen 12**.

Due to the constitution that the cross-sectional area of the resin forming the first shaft 10 is larger than the cross-sectional area of either the first lumen 11 or the second lumen 12, which has a larger cross-sectional area, in the cross section perpendicular to the longitudinal direction, the optical fiber 40 is joined to the distal end 11*d* of the first lumen 11, the proximal end 30*p* of the balloon 30 is joined to the second shaft 20, and the distal end 30*d* of the balloon 30 is joined to the optical fiber 40, whereby the proximal end 30*p* of the balloon 30 comes to be connected to the first shaft 10 via the second shaft 20, and the distal end 30*d* of the balloon 30 comes to be connected to the first shaft 10 via the optical fiber 40, the force for pulling the first shaft 10 is easily transmitted to both the proximal end 30*p* and the distal end 30*d* of the balloon 30. Therefore, it is possible to improve removability of the balloon catheter 1 when the balloon catheter 1 is removed from an endoscope or the like.

Since the optical fiber 40 is joined to the distal end 11*d* of the first lumen 11, the proximal end 30*p* of the balloon 30 is joined to the second shaft 20, and the distal end 30*d* of the balloon 30 is joined to the optical fiber 40, the optical fiber 40 comes to be joined to the distal end 11*d* of the first lumen 11, that is located proximal to the proximal end 30*p* of the balloon 30. Therefore, in the longitudinal direction of the balloon catheter 1, the optical fiber 40 is not fixed to another object between the distal end 30*d* of the balloon 30 and the distal end 11*d* of the first lumen 11, and the optical fiber 40 is able to freely change its position or bend according to a bent state of the balloon catheter 1. As a result, in irradiating a target tissue with light to perform photodynamic therapy, the optical fiber 40 can be arranged at a center of the balloon 30 in the cross section perpendicular to the longitudinal direction, which makes it easier to perform photodynamic therapy.

The proximal end 30*p* of the balloon 30 is preferably joined to the distal end 20*d* of the second shaft 20, and the distal end 30*d* of the balloon 30 is preferably joined to the distal end 40*d* of the optical fiber 40.

In joining between the optical fiber 40 and the first lumen 11, joining between the balloon 30 and the second shaft 20, and joining between the balloon 30 and the optical fiber 40, each may be directly joined to each other or may be joined via another member. Examples of a method for joining between the optical fiber 40 and the first lumen 11, joining between the balloon 30 and the second shaft 20, and joining between the balloon 30 and the optical fiber 40 include, for example, welding, adhesion, and others.

In the present invention, a proximal side refers to a user's side, that is, an operator's hand side, with respect to the longitudinal direction of the first shaft 10, and a distal side refers to an opposite side of the distal side, that is, a treatment target side. Further, a direction from the proximal side to the distal side of the first shaft 10 or a direction from the distal side to the proximal side of that is referred to as a longitudinal direction. The longitudinal direction can be rephrased as a distal-proximal direction of the first shaft 10.

As shown in FIG. 1, the first shaft 10 extends in the longitudinal direction and has a tubular structure having the first lumen 11 and the second lumen 12. In the first lumen 11, the distal end 11*d* of the first lumen 11 is joined to the optical fiber 40, and inside the first lumen 11, the optical fiber 40 can be disposed. The second lumen 12 is connected to a lumen of the balloon 30 and can serve as a path for supplying fluid to the inside of the balloon 30.

As shown in FIG. 1, at a joint part between the distal end 11*d* of the first lumen 11 and the optical fiber 40, it is preferable that there is no gap where the first lumen 11 is communicated to the outside of the first lumen 11. That is, the optical fiber 40 is preferably joined to the first lumen 11 so as to seal the distal end 11*d* of the first lumen 11. When the joint part between the distal end 11*d* of the first lumen 11 and the optical fiber 40 does not have a gap in which the first lumen 11 is communicated to the outside of the first lumen 11, the fluid supplied through the second lumen 12 is prevented from entering the first lumen 11. As a result, the balloon 30 can be expanded quickly, so that the time required for expansion of the balloon 30 can be shortened, and the procedure time can be shortened.

The first shaft 10 only have to have at least the first lumen 11 and the second lumen 12, and may further have another lumen that is different from the first lumen 11 and the second lumen 12.

It is preferable that the first shaft 10 has flexibility. When the first shaft 10 has flexibility, the first shaft 10 is made to be flexible and easy to bend. Therefore, it becomes easy to insert the balloon catheter 1 into a human body.

A material constituting the first shaft 10 is a resin, and as shown in FIG. 2, the cross-sectional area of the resin forming the first shaft 10 is larger than the cross-sectional area of either the first lumen 11 or the second lumen 12, which has a larger cross-sectional area, in the cross section perpendicular to the longitudinal direction. Specifically, for example in the balloon catheter 1 shown in FIG. 2, since the cross-sectional area of the second lumen 12 is larger than the cross-sectional area of the first lumen 11, the cross-sectional area of the resin forming the first shaft 10 is compared with the cross-sectional area of the second lumen 12. In the case where the cross-sectional area of the first lumen 11 and the cross-sectional area of the second lumen 12 are the same, either the cross-sectional area of the first lumen 11 or the cross-sectional area of the second lumen 12 may be used for comparison with the cross-sectional area of the resin forming the first shaft 10. Since the cross-sectional area of the resin forming the first shaft 10 is larger than the cross-sectional area of either the first lumen 11 or the second lumen 12, which has a large cross-sectional area, rigidity of the first shaft 10 can be increased. As a result, the force for pushing the balloon catheter 1 when inserting the balloon catheter 1 or the force for pulling the balloon catheter 1 when removing the balloon catheter 1 is applied to the first shaft 10, the force can be easily transmitted to the distal end 30*d* and the proximal end 30*p* of the balloon 30 through the first shaft 10, whereby removability of the balloon catheter 1 can be improved.

In the cross section perpendicular to the longitudinal direction, the cross-sectional area of the resin forming the first shaft 10 is preferably 1.1 times or more, more preferably 1.2 times or more, and even more preferably 1.3 times or more the cross-sectional area of either the first lumen 11 or the second lumen 12, which has a larger cross-sectional area. By setting the lower limit of the ratio between the cross-sectional area of the resin forming the first shaft 10 and the cross-sectional area of either one having a larger cross-sectional area of the first lumen 11 and the second lumen 12, it is possible to sufficiently increase the rigidity of the first shaft 10. The cross-sectional area of the resin forming the first shaft 10 is preferably 5 times or less, more preferably 4 times or less, and even more preferably 3 times or less the cross-sectional area of either the first lumen 11 or the second lumen 12, which has a larger cross-sectional area. By setting the upper limit of the ratio between the cross-sectional area of the resin forming the first shaft 10 and the cross-sectional area of either one having a larger cross-sectional area of the first lumen 11 and the second lumen 12, the areas of the first lumen 11 and the second lumen 12 possessed by the first shaft 10 can be secured, and the optical fiber 40 can be smoothly inserted into the first lumen 11 and the fluid for expanding the balloon 30 can be smoothly supplied to and removed from the second lumen 12.

Examples of the material constituting the first shaft 10 include, for example, synthetic resins including a polyolefin resin such as polyethylene and polypropylene, a polyamide resin such as nylon, a polyester resin such as PET, an aromatic polyether ketone resin such as PEEK, a vinyl chloride resin, a polyether polyamide resin, a polyurethane resin, a polyimide resin, a fluororesin such as PTFE, PFA, ETFE. These may be used alone or in combination of two or more. Among them, the material constituting the first shaft 10 preferably includes a polyolefin resin, a polyamide resin or a fluororesin. When the material constituting the first shaft 10 includes a polyolefin resin, a polyamide resin or a fluororesin, the first shaft 10 has flexibility and slipperiness of the surface of the first shaft 10 is improved, and therefore, the balloon catheter 1 having good insertability can be obtained.

As shown in FIG. 1, the second shaft 20 extends in the longitudinal direction and has a tubular structure having a lumen. The second shaft 20 is located on a distal side of the first shaft 10. That is, the second shaft 20 is located distal to a distal end **10*d* of the first shaft 10. The optical fiber 40 is disposed in the lumen of the second shaft 20. The second shaft 20 preferably has flexibility. When the second shaft 20 has flexibility, the second shaft 20 is made to be flexible, and it becomes possible to enhance the insertability of the balloon catheter 1**.

The second shaft 20 may be composed of a plurality of members, however, it is preferably composed of single tubular member. When the second shaft 20 is composed of single tubular member, the second shaft 20 becomes flexible. As a result, when the balloon catheter 1 is inserted into a bent internal lumen, the second shaft 20 is easily bent, and the insertability of the balloon catheter 1 can be enhanced.

Examples of the material constituting the second shaft 20 includes, for example, synthetic resins including a polyolefin resin such as polyethylene and polypropylene, a polyamide resin such as nylon, a polyester resin such as PET, an aromatic polyether ketone resin such as PEEK, a vinyl chloride resin, a polyether polyamide resin, a polyurethane resin, a polyimide resin, a fluororesin such as PTFE, PFA, ETFE; and metals such as stainless steel, carbon steel and nickel titanium alloy. These may be used alone or in combination of two or more. Among them, it is preferable that the material constituting the second shaft 20 contains the same material as the material constituting the first shaft 10. When the material constituting the second shaft 20 contains the same material as the material constituting the first shaft 10, physical properties such as hardness and surface slipperiness of the first shaft 10 and the second shaft 20 come to be similar to each other, and the balloon catheter 1 having good insertability into a human body can be obtained. Further, in directly joining the first shaft 10 and the second shaft 20 to each other, the joining strength between the first shaft 10 and the second shaft 20 can be increased.

The balloon 30 is located on a distal side of the second shaft 20. That is, the balloon 30 is located distal to the distal end **20*d* of the second shaft 20. Further, the proximal end 30*p* of the balloon 30 is joined to the second shaft 20, and the distal end 30*d* of the balloon 30 is joined to the optical fiber 40. The proximal end 30*p* of the balloon 30 is preferably joined to the distal end 20*d* of the second shaft 20**.

The balloon 30 is configured so that fluid is supplied to the inside of the balloon 30 from a fluid feeder through the first shaft 10 and the second shaft 20. By supplying the fluid inside the balloon 30, the balloon 30 can be expanded. Further, the balloon 30 can be contracted by removing the fluid inside the balloon 30 from the balloon 30. When the balloon 30 is expanded, the outer surface of the balloon 30 comes into contact with a vessel wall of an internal lumen such as a blood vessel or a digestive tract, so that the balloon 30 can be fixed in the human body. The fluid supplied to the inside of the balloon 30 may be a pressure fluid compressed by a pump or the like.

As the type of the fluid supplied into the balloon 30, a liquid such as physiological saline, a contrast agent and a mixed solution thereof, or a gas such as air, nitrogen and carbon dioxide can be used, for example. Among them, a gas is preferably used as the fluid supplied into the balloon 30. When the fluid supplied into the balloon 30 is a gas, the fluid existing in the balloon 30 is less likely to interfere with emitted light of the optical fiber 40 disposed inside the balloon 30 when performing photodynamic therapy.

As shown in FIG. 1, the balloon 30 preferably has a straight pipe portion 31. When the balloon 30 has the straight pipe portion 31, the area where the balloon 30 is in contact with a luminal wall in a human body can be increased. Therefore, the balloon 30 can be fixed in a lumen of the human body, and photodynamic therapy can be easily conducted.

It is preferable that the balloon 30 has a proximal tapered portion connected to the straight pipe portion 31 on a proximal side of the proximal end **31*p* of the straight pipe portion 31 and a distal tapered portion connected to the straight pipe portion 31 on a distal side of the distal end 31*d* of the straight pipe portion 31, and the proximal tapered portion and the distal tapered portion are formed so as to reduce the diameter as a distance from the straight pipe portion 31 increases. When the balloon 30 has the proximal tapered portion and the distal tapered portion configured so that the diameter of the balloon 30 reduces as the distance from the straight pipe portion 31 increases, strength of the balloon 30 can be increased, and the balloon 30 is less likely to be damaged when a force is applied to the balloon 30. In addition, since the step generated when the balloon 30 is wound around the shaft can be reduced, the balloon 30 can be easily inserted into a lumen in the human body. The balloon 30 can be configured so that the portions from the proximal tapered portion via the straight pipe portion 31 to the distal tapered portion are swollen by supplying the fluid. In the present invention, an expansionable portion is regarded as the balloon 30**.

Examples of the material constituting the balloon 30 include, for example, a polyolefin resin such as polyethylene, polypropylene and an ethylene-propylene copolymer, a polyester resin such as polyethylene terephthalate and a polyester elastomer, a polyurethane resin such as polyurethane and a polyurethane elastomer, a polyphenylene sulfide resin, a polyamide resin such as a polyamide and a polyamide elastomer, a vinyl chloride resin, a fluororesin, a silicone resin, and a natural rubber such as latex rubber. These may be used alone or in combination of two or more. Among them, the material constituting the balloon 30 is preferably a polyamide resin, a polyester resin or a polyurethane resin. When the material constituting the balloon 30 is a polyamide resin, a polyester resin or a polyurethane resin, it is possible to reduce a thickness of the balloon 30 and improve its flexibility.

As shown in FIG. 1, the optical fiber 40 extends in the longitudinal direction. The optical fiber 40 is disposed inside the balloon 30 and is joined to the distal end 11*d* of the first lumen 11. The optical fiber 40 is a transmission path that transmits an optical signal to a target tissue. Although it is not shown the drawings, the optical fiber 40 is connected to a light source such as a semiconductor laser via a connector or the like provided on a proximal end thereof. The optical fiber 40 includes a core and a clad that covers an outer side of the core in a radial direction. As materials constituting the core and the clad, synthetic resins such as a fluororesin and an acrylic resin, and glass such as quartz glass and fluoride glass can be used, for example.

It is preferable that the optical fiber 40 has a non-existent region of the clad in a part on a distal portion of the core. The non-existent region of the clad refers to a portion where the clad does not exist in at least a part in a circumferential direction of the core, and provides a light emitting area in the optical fiber 40. When the optical fiber 40 has the non-existent region of the clad, the balloon catheter 1 is configured to be a side-irradiation type one used for photodynamic therapy.

The position, with respect to the longitudinal direction, where the non-existing region of the clad is provided is not particularly limited as long as it is a part of a distal portion of the core, however, it is preferable that the non-existing region of the clad is provided at a portion including a distal end of the core. When the non-existent region of the clad is provided at the portion including the distal end of the core, forming the non-existent region of the clad is facilitated.

The non-existent region of the clad can be formed by peeling the clad by, for example, etching or polishing. Further, it is more preferable to roughen the outer surface of the non-existent region of the clad by a method such as sanding. By roughening the outer surface of the non-existent region of the clad, light diffusivity can be improved.

Examples of a method for joining the optical fiber 40 to the first lumen 11 include, for example, welding, bonding with an adhesive, and others. Further, although it is not shown in the drawings, the optical fiber 40 may be further provided with a covering material. In the case where the optical fiber 40 is provided with a covering material, preferable examples of the material constituting the covering material include synthetic resin including, for example, a polyolefin resin such as polyethylene and polypropylene, a polyamide resin such as nylon, a polyester resin such as PET, an aromatic polyether ketone resin such as PEEK, a vinyl chloride resin, a polyether polyamide resin, a polyurethane resin, a polyimide resin, and a fluororesin such as PTFE, PFA, ETFE, in view of bondability with the first lumen 11.

Since the balloon catheter 1 comprises the optical fiber 40 and the optical fiber 40 is disposed inside the balloon 30, light emitted from the optical fiber 40 tends to go toward the straight pipe portion 31 of the balloon 30. Therefore, it becomes easy to irradiate a target tissue with the light used for photodynamic therapy via the optical fiber 40, and the photodynamic therapy can be efficiently performed.

As shown in FIG. 1, it is preferable that the distal end 40*d* of the optical fiber 40 is located distal to the distal end 30*d* of the balloon 30. When the distal end 40*d* of the optical fiber 40 is located distal to the distal end 30*d* of the balloon 30, rigidity of a distal end part of the balloon catheter 1 is increased. Therefore, it becomes easy to insert the balloon catheter 1 into a human body. Further, when the distal end 40*d* of the optical fiber 40 is located distal to the distal end 30*d* of the balloon 30, the optical fiber 40 comes to be present over the entire length of the balloon 30 in the longitudinal direction. As a result, the optical fiber 40 can be present in the entire straight pipe portion 31 of the balloon 30 in the longitudinal direction, which facilitates photodynamic therapy.

At a cutting edge of the optical fiber 40, the light intensity is low and may not be sufficient for photodynamic therapy. For supplying a sufficient amount of light to the balloon 30, the distal end 40*d* of the optical fiber 40 is preferably located distal to the straight pipe portion 31 of the balloon 30 or distal to the distal tapered portion of the balloon 30. When the distal end 40*d* of the optical fiber 40 is located distal to the straight pipe portion 31 or distal to the distal tapered portion of the balloon 30, an enough amount of the light for photodynamic therapy can be secured. Further, in such a case that the light is to be supplied to the straight pipe portion 31 of the balloon 30 from the optical fiber 40 and is not to be supplied to the tapered portion of the balloon 30, it is possible to irradiate a desired site with light by appropriately arranging a covering material on the optical fiber 40 or by another means.

It is preferable that the distal end 40*d* of the optical fiber 40 is located distal to the distal tapered portion of the balloon 30. When the distal end 40*d* of the optical fiber 40 is located distal to the distal tapered portion of the balloon 30, the amount of the light for photodynamic therapy can be sufficiently secured. Further, as the distal end 40*d* of the optical fiber 40 is located distal to the distal end 30*d* of the balloon 30, rigidity of the distal end part of the balloon catheter 1 is increased. Therefore, it becomes easy to insert the balloon catheter 1 into a human body.

Although it is not shown in the drawings, it is preferable that the balloon catheter 1 comprises a handle portion on a proximal side thereof. The handle portion preferably has a longitudinally extending lumen which is connected to the first lumen 11. The lumen which the handle portion has and which is connected to the first lumen 11 can be used as an insertion path for the optical fiber 40 or the like. Further, it is preferable that the handle portion has a lumen which is provided with a fluid injection port and is connected to the second lumen 12. The lumen which the handle has and which is connected to the second lumen 12 can be used as a fluid supply and removal path for expanding the balloon 30.

It is preferable that the proximal end 20*p* of the second shaft 20 is joined to the distal end 10*d* of the first shaft 10. That is, it is preferable that the first shaft 10 and the second shaft 20 are directly joined. When the proximal end 20*p* of the second shaft 20 is joined to the distal end 10*d* of the first shaft 10, it becomes easier to join the second shaft 20 to the first shaft 10. As a result, the efficiency of manufacturing the balloon catheter 1 can be enhanced.

Next, a second balloon catheter of the present invention is explained. In the following description of the second balloon catheter, the explanation overlapping with the above explanation is omitted.

Figure 3:
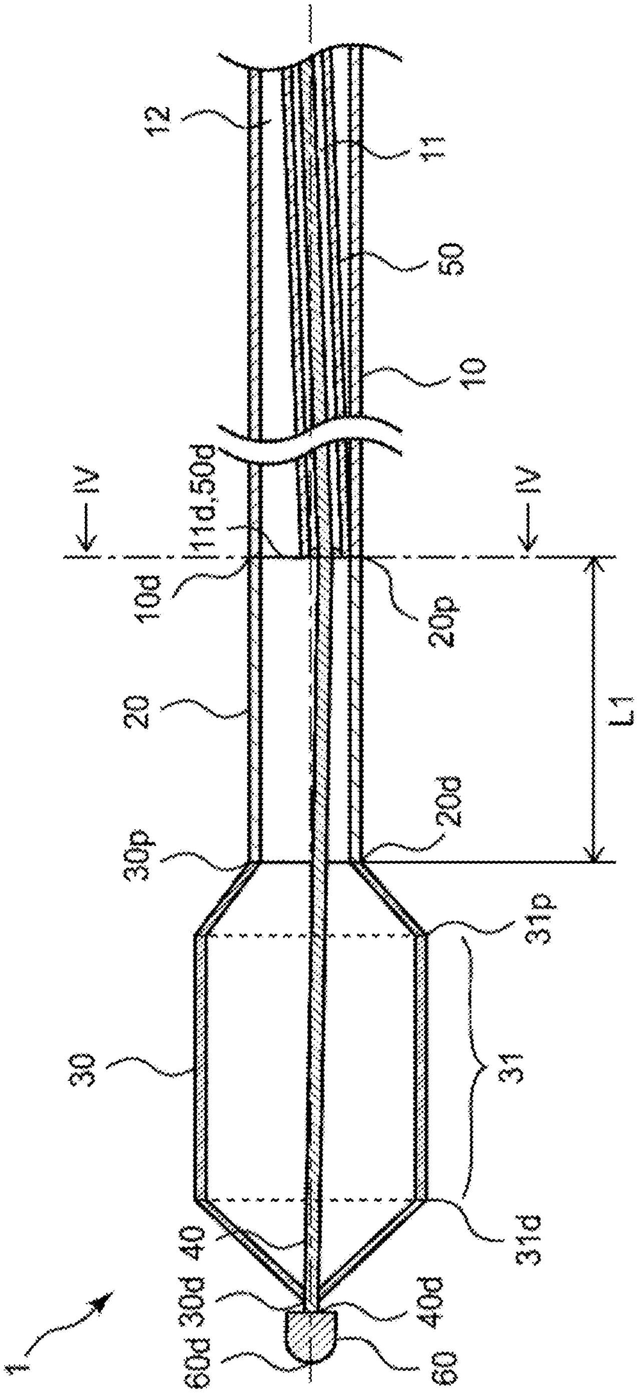
FIG. 3 shows a cross-sectional view of a second balloon catheter along a longitudinal direction according to an embodiment of the present invention.

FIG. 3 shows a cross-sectional view of a second balloon catheter 1 along the longitudinal direction according to an embodiment of the present invention, and FIG. 4 shows a cross-sectional view taken along a line IV-IV, that is perpendicular to the longitudinal direction, of the balloon catheter 1 shown in FIG. 3. As shown in FIGS. 3 and 4, a first shaft 10 of the balloon catheter 1 includes an inner tube 50 having a first lumen 11 and has a second lumen 12, and at least a part of an outer surface of the inner tube 50 is fixed to an inner surface of the first shaft 10.

The first shaft 10 is provided with the inner tube 50 having the first lumen 11 and has the second lumen 12, at least a part of the outer surface of the inner tube 50 is fixed to the inner surface of the first shaft 10, an optical fiber 40 is joined to a distal end 50*d* of the inner tube 50, a proximal end 30*p* of a balloon 30 is joined to a second shaft 20, and a distal end 30*d* of the balloon 30 is joined to the optical fiber 40; whereby the proximal end 30*p* of the balloon 30 comes to be connected to the first shaft 10 via the second shaft 20, and the distal end 30*d* of the balloon 30 comes to be connected to the first shaft 10 via the optical fiber 40. As a result, when removing the balloon catheter 1 from an endoscope or the like, the force for pulling the first shaft 10 is easily transmitted to both the distal end 30*d* and the proximal end 30*p* of the balloon 30, thereby improving removability of the balloon catheter 1. The proximal end 30*p* of the balloon 30 is preferably joined to a distal end 20*d* of the second shaft 20, and the distal end 30*d* of the balloon 30 is preferably joined to a distal end 40*d* of the optical fiber 40.

Further, since the optical fiber 40 is joined to the distal end 50*d* of the inner tube 50, the proximal end 30*p* of the balloon 30 is joined to the second shaft 20, and the distal end 30*d* of the balloon 30 is joined to the optical fiber 40, the optical fiber 40 is not fixed to another object between the distal end 30*d* of the balloon 30 and the distal end 11*d* of the first lumen 11 in the longitudinal direction of the balloon catheter 1, and the optical fiber 40 is able to freely change its position or bend according to a bent state of the balloon catheter 1. Therefore, in irradiating a target tissue with light to perform photodynamic therapy, the optical fiber 40 can be arranged at a center of the balloon 30 in the cross section perpendicular to the longitudinal direction, which makes it easier to perform photodynamic therapy.

As shown in FIG. 3, the inner tube 50 extends in the longitudinal direction. The optical fiber 40 is inserted into a lumen of the inner tube 50.

Examples of a method for fixing at least a part of the outer surface of the inner tube 50 to the inner surface of the first shaft 10 include, for example, welding, adhesion, fixing via another object, and others.

As shown in FIGS. 1 and 3, it is preferable that the length L1 of the second shaft 20 in the longitudinal direction is 10 times or more a minimum outer diameter of the second shaft 20. The length L1 of the second shaft 20 in the longitudinal direction indicates a distance between the distal end 20*d* of the second shaft 20 and the proximal end 20*p* of the second shaft 20 in the longitudinal direction. When the length L1 of the second shaft 20 is 10 times or more the minimum outer diameter of the second shaft 20, the length L1 of the second shaft 20 can be sufficiently secured, and the distance between the distal end 30*d* of the balloon 30, which is joined to the optical fiber 40, and the distal end 11*d* of the first lumen 11, which is joined to the optical fiber 40, can be increased. That is, the distance between the two points where the optical fiber 40 is joined to another object can be increased, and the optical fiber 40 is able to freely change its position or bend according to a bent state of the balloon catheter 1 at a portion where the optical fiber 40 is not joined to another object. As a result, the optical fiber 40 is positioned at a center of the balloon 30 in the cross section perpendicular to the longitudinal direction, which makes it possible to efficiently perform photodynamic therapy.

The length L1 of the second shaft 20 in the longitudinal direction is preferably 10 times or more the minimum outer diameter of the second shaft 20, more preferably 11 times or more the minimum outer diameter of the second shaft 20, and even more preferably 12 times or more the minimum outer diameter of the second shaft 20. By setting the lower limit of the ratio of the length L1 of the second shaft 20 to the minimum outer diameter of the second shaft 20 in the above range, the distance between the distal end 30*d* of the balloon 30, which is joined to the optical fiber 40, and the distal end 11*d* of the first lumen 11, which is joined to the optical fiber 40, can be sufficiently secured. The upper limit of the ratio of the length L1 of the second shaft 20 to the minimum outer diameter of the second shaft 20 can be, for example, 600 times or less, 400 times or less, or 200 times or less.

As shown in FIG. 4, in a cross section perpendicular to the longitudinal direction at the proximal end 20*p* of the second shaft 20, the position of a central axis C20 of the outer shape of the second shaft 20 is different from the position of a central axis C40 of the outer shape of the optical fiber 40. When the position of the central axis C20 of the outer shape of the second shaft 20 is different from the position of the central axis C40 of the outer shape of the optical fiber 40, the optical fiber 40 is easily freely change its position or bend in the respective lumens of the second shaft 20 and the balloon 30. Therefore, in inserting the balloon catheter 1 into a bent internal lumen, the optical fiber 40 is easy to move according to a bent state of the balloon catheter 1, and it becomes easy that the optical fiber 40 is located at a center of the balloon 30 in the cross section perpendicular to the longitudinal direction. As a result, photodynamic therapy is easily performed.

As shown in FIG. 4, in the cross section perpendicular to the longitudinal direction of the second shaft 20, a cross-sectional area of a gap between the inner surface of the second shaft 20 and the outer surface of the optical fiber 40 is preferably 40% or more of a cross-sectional area of the lumen of the second shaft 20. When the cross-sectional area of the gap between the inner surface of the second shaft 20 and the outer surface of the optical fiber 40 is 40% or more of the cross-sectional area of the lumen of the second shaft 20, the optical fiber 40 can move freely in the second shaft 20. Therefore, even when the second shaft 20 is in a bent state, the optical fiber 40 is likely to be located at a center of the balloon 30 in the cross section perpendicular to the longitudinal direction, and photodynamic therapy is easily performed.

In the cross section perpendicular to the longitudinal direction of the second shaft 20, the cross-sectional area of the gap between the inner surface of the second shaft 20 and the outer surface of the optical fiber 40 is preferably 40% or more, more preferably 45% or more, and even more preferably 50% or more of the cross-sectional area of the lumen of the second shaft 20. By setting the lower limit of the ratio between the cross-sectional area of the gap between the inner surface of the second shaft 20 and the outer surface of the optical fiber 40 and the cross-sectional area of the lumen of the second shaft 20 in the above range, it becomes easy for the optical fiber 40 to move freely in the lumen of the second shaft 20. The upper limit of the ratio between the cross-sectional area of the gap between the inner surface of the second shaft 20 and the outer surface of the optical fiber 40 and the cross-sectional area of the lumen of the second shaft 20 can be, for example, 99% or less, 97% or less, or 95% or less.

FIG. 5 shows a cross-sectional view of the second shaft 20 along a direction perpendicular to the longitudinal direction in the balloon catheter 1 according to another embodiment of the present invention. As shown in FIG. 5, it is preferable that a protrusion 70 which comes into contact with the outer surface of the optical fiber 40 is provided on the inner surface of the second shaft 20. By providing the protrusion 70 on the inner surface of the second shaft 20, the protrusion 70 can serve to determine a position of the optical fiber 40 in the second shaft 20. As a result, the position of the optical fiber 40 can be regulated so as not to deviate significantly from the central axis of the balloon 30. The protrusion 70 is not fixed to the optical fiber 40.

The protrusion 70 is preferably disposed on the inner surface of a distal end part of the second shaft 20. By arranging the protrusion 70 which comes into contact with the outer surface of the optical fiber 40 on the inner surface of the distal end part of the second shaft 20 so that the optical fiber 40 is placed at the center of the second shaft 20 in the cross section perpendicular to the longitudinal direction, the position of the optical fiber 40 tends to be set at the center of the second shaft 20 at the distal end part of the second shaft 20. As a result, also in the lumen of the balloon 30 which is located distal to the second shaft 20 and is joined to the second shaft 20, the position of the optical fiber 40 tends to be located at the center of the balloon 30, and the balloon catheter 1 suitable for photodynamic therapy can be obtained.

It is preferable that the number of the protrusion 70 disposed on the inner surface of the second shaft 20 is a plurality. When the number of the protrusion 70 is plurality, the position of the optical fiber 40 in the second shaft 20 can be easily regulated by the protrusions 70.

As shown in FIGS. 1 and 3, it is preferable that a tip piece 60 is provided on a distal side of the optical fiber 40, and a distal end 60*d* of the tip piece 60 is located distal to the distal end 30*d* of the balloon 30. When the distal end 60*d* of the tip piece 60 is located distal to the distal end 30*d* of the balloon 30, rigidity of the distal end part of the balloon catheter 1 is increased. As a result, it is possible to enhance insertability of the balloon catheter 1.

In the case where the tip piece 60 is provided on the distal side of the optical fiber 40, the color of the tip piece 60 is preferably different from the color of the optical fiber 40. That the color of the tip piece 60 is different from the color of the optical fiber 40 means that at least one of the hue, lightness, and saturation defined in JIS Z8721 is different. When the color of the tip piece 60 is different from the color of the optical fiber 40, the tip piece 60 can be easily visible under an endoscope. As a result, it becomes easy to confirm the positions of the tip piece 60 and the balloon 30 in the lumen of a human body.

As described above, the balloon catheter of the present invention comprises: a first shaft having a first lumen and a second lumen; a second shaft located distal to the first shaft; a balloon located distal to the second shaft; and an optical fiber disposed inside the balloon; wherein: the first shaft is made of a resin; a cross-sectional area of the resin forming the first shaft is larger than a cross-sectional area of either the first lumen or the second lumen, which has a larger cross-sectional area, in a cross section perpendicular to a longitudinal direction; the optical fiber is joined to a distal end of the first lumen; a proximal end of the balloon is joined to the second shaft; and a distal end of the balloon is joined to the optical fiber. Since the cross-sectional area of the resin forming the first shaft is larger than the cross-sectional area of either the first lumen or the second lumen, which has a larger cross-sectional area, in a cross section perpendicular to the longitudinal direction, the optical fiber is joined to the distal end of the first lumen, the proximal end of the balloon is joined to the second shaft, and the distal end of the balloon is joined to the optical fiber, the force applied to the balloon catheter is easily transmitted to both the proximal end and the distal end of the balloon. Therefore, it is possible to improve removability of the balloon catheter from an endoscope or the like. In addition, since the optical fiber is joined to the distal end of the first lumen, that is not the proximal end of the balloon and is located proximal to the proximal end of the balloon, the optical fiber is not fixed to another object between the distal end of the balloon and the distal end of the first lumen in the longitudinal direction, and is able to move freely. As a result, in irradiating a target tissue with light to perform photodynamic therapy, the optical fiber can be arranged at a center of the balloon in the cross section perpendicular to the longitudinal direction, even in the state where the shaft of the balloon catheter is bent or the balloon is compressed, which facilitate photodynamic therapy.

Further, the second balloon catheter of the present invention comprises: a first shaft provided with an inner tube having a first lumen, and having a second lumen; a second shaft located distal to the first shaft; a balloon located distal to the second shaft; and an optical fiber disposed inside the balloon; wherein: at least a part of an outer surface of the inner tube is fixed to an inner surface of the first shaft; the optical fiber is joined to a distal end of the inner tube; a proximal end of the balloon is joined to the second shaft; and a distal end of the balloon is joined to the optical fiber. Since the first shaft is provided with the inner tube having the first lumen and has second lumen, at least a part of the outer surface of the inner tube is fixed to the inner surface of the first shaft, the optical fiber is joined to the distal end of the inner tube, the proximal end of the balloon is joined to the second shaft, and the distal end of the balloon is joined to the optical fiber, the force for pulling the balloon catheter is easily transmitted to both the proximal end and the distal end of the balloon when the balloon catheter is removed from an endoscope or the like, which makes it easier to remove the balloon catheter from an endoscope or the like. Further, since the optical fiber is joined to the distal end of the first lumen, the optical fiber is able to move freely in the range between the distal end of the balloon and the distal end of the first lumen in the longitudinal direction. As a result, the optical fiber can be arranged at a center of the balloon in the cross section perpendicular to the longitudinal direction, even in the state where the shaft of the balloon catheter is bent or the balloon is compressed.

This application claims priority to Japanese Patent Application No. 2020-039082, filed on Mar. 6, 2020. All of the contents of the Japanese Patent Application No. 2020-039082, filed on Mar. 6, 2020, are incorporated by reference herein.

REFERENCE SIGNS LIST

1: balloon catheter
10: first shaft
10*d*: distal end of first shaft
11: first lumen
11*d*: distal end of first lumen
11*p*: proximal end of first lumen
12: second lumen
20: second shaft
20*d*: distal end of second shaft
20*p*: proximal end of second shaft
30: balloon
30*d*: distal end of balloon
30*p*: proximal end of balloon
31: straight pipe portion

31*d*: distal end of straight pipe portion
31*p*: proximal end of straight pipe portion
40: optical fiber
40*d*: distal end of optical fiber
50: inner tube
50*d*: distal end of inner tube
60: tip piece
60*d*: distal end of tip piece
70: protrusion
L1: length of second shaft
C20: central axis of outer shape of second shaft
C40: central axis of outer shape of optical fiber

The invention claimed is:

1. A balloon catheter extending in a longitudinal direction from a proximal side to a distal side comprising:
a first shaft having a first lumen and a second lumen;
a second shaft located distal to the first shaft;
a balloon located distal to the second shaft; and
an optical fiber disposed inside the balloon, wherein
the first shaft is made of a resin,
a cross-sectional area of the resin forming the first shaft is larger than each of cross-sectional areas of the first lumen and the second lumen in a cross section perpendicular to the longitudinal direction,
the optical fiber is joined to a distal end of the first lumen to seal the distal end of the first lumen so that there is no gap at a joint portion between the distal end of the first lumen and the optical fiber, and the first lumen is not communicated with the second lumen through the joint portion,
a proximal end of the balloon is joined to the second shaft, and
a distal end of the balloon is joined to the optical fiber.

2. A balloon catheter extending in a longitudinal direction from a proximal side to a distal side comprising:
an inner tube having a first lumen;
a first shaft, in which the inner tube is provided so that the first lumen and a second lumen are formed in the first shaft;
a second shaft located distal to the first shaft;
a balloon located distal to the second shaft; and
an optical fiber disposed inside the balloon, wherein
at least a part of an outer surface of the inner tube is fixed to an inner surface of the first shaft,
the optical fiber is joined to a distal end of the first lumen of the inner tube to seal the distal end of the first lumen so that there is no gap at a joint portion between the distal end of the first lumen and the optical fiber, and the first lumen is not communicated with the second lumen through the joint portion,
a proximal end of the balloon is joined to the second shaft, and
a distal end of the balloon is joined to the optical fiber.

3. The balloon catheter according to claim 1, wherein
a length of the second shaft in the longitudinal direction is 10 times or more a minimum outer diameter of the second shaft.

4. The balloon catheter according to claim 1, wherein
the optical fiber is disposed in a lumen of the second shaft so that a position of a central axis of an outer shape of the second shaft is different from a position of a central axis of an outer shape of the optical fiber in a cross section perpendicular to the longitudinal direction at a proximal end of the second shaft.

5. The balloon catheter according to claim 1, wherein
an area of a gap between an inner surface of the second shaft and an outer surface of the optical fiber is 40% or more of an area of a lumen of the second shaft in a cross section perpendicular to the longitudinal direction of the second shaft.

6. The balloon catheter according to claim 1, wherein
a protrusion is provided on an inner surface of the second shaft so that the protrusion comes into contact with an outer surface of the optical fiber.

7. The balloon catheter according to claim 1, wherein
a tip piece is provided on a distal side of the optical fiber, and
a distal end of the tip piece is located distal to the distal end of the balloon.

8. The balloon catheter according to claim 2, wherein
a length of the second shaft in the longitudinal direction is 10 times or more a minimum outer diameter of the second shaft.

9. The balloon catheter according to claim 2, wherein
the optical fiber is disposed in a lumen of the second shaft so that a position of a central axis of an outer shape of the second shaft is different from a position of a central axis of an outer shape of the optical fiber in a cross section perpendicular to the longitudinal direction at a proximal end of the second shaft.

10. The balloon catheter according to claim 2, wherein
an area of a gap between an inner surface of the second shaft and an outer surface of the optical fiber is 40% or more of an area of a lumen of the second shaft in a cross section perpendicular to the longitudinal direction of the second shaft.

11. The balloon catheter according to claim 2, wherein
a protrusion is provided on an inner surface of the second shaft so that the protrusion comes into contact with an outer surface of the optical fiber.

12. The balloon catheter according to claim 2, wherein
a tip piece is provided on a distal side of the optical fiber, and
a distal end of the tip piece is located distal to the distal end of the balloon.

13. The balloon catheter according to claim 1, wherein the second lumen is communicated with a lumen of the balloon.

14. The balloon catheter according to claim 2, wherein the second lumen is communicated with a lumen of the balloon.

* * * * *